US006268522B1

(12) United States Patent
Hagemeyer et al.

(10) Patent No.: US 6,268,522 B1
(45) Date of Patent: Jul. 31, 2001

(54) CATALYST, PROCESS FOR ITS PRODUCTION AND ITS USE FOR PREPARING VINYL ACETATE

(75) Inventors: Alfred Hagemeyer, Sunnyvale, CA (US); Uwe Dingerdissen, Seeheim-Jugenheim; Klaus Kühlein, Kelkheim, both of (DE); Johannes Heitz, Linz (AT); Dieter Bäuerle, Altenberg (AT)

(73) Assignee: Celanese GmbH, Frankfurt (DE)

( * ) Notice: Subject to any disclaimer, the term of this patent is extended or adjusted under 35 U.S.C. 154(b) by 0 days.

(21) Appl. No.: 09/089,627

(22) Filed: Jun. 3, 1998

(30) Foreign Application Priority Data

Jun. 5, 1997 (DE) .............................................. 197 23 591

(51) Int. Cl.⁷ ............................. C07C 67/05; B01J 31/00
(52) U.S. Cl. ......................... 560/245; 502/330; 502/170; 204/157.41
(58) Field of Search .................................... 502/170, 330; 560/245; 207/157.41

(56) References Cited

U.S. PATENT DOCUMENTS 3,627,821 * 12/1971 Sennewald et al. .
4,264,421   4/1981 Bard et al. .
5,185,308   2/1993 Bartley et al. .
5,260,108  11/1993 Braren et al. .

\* cited by examiner

Primary Examiner—Gary Geist
Assistant Examiner—Robert W. Deemie
(74) Attorney, Agent, or Firm—Frommer Lawrence & Haug LLP

(57) ABSTRACT

The invention relates to a process for producing supported shell catalysts comprising noble metals by UV photoreduction of noble metal salt precursors fixed to a support. For this purpose, the shaped supported body is impregnated with suitable noble metal salts which are then reduced to the metals in a zone close to the surface by means of UV radiation, preferably in the absence of a chemical reducing agent. The metal salts in the interior of the pellets which have not been irradiated and therefore have not been reduced are extracted using a solvent.

The noble metal shell catalysts produced in this way can be used for many heterogeneously catalyzed reactions such as hydrogenations and oxidations.

According to the invention, Pd/Au shell catalysts on porous ceramic supports, e.g. $SiO_2$ shaped bodies, produced by this process can be used in the synthesis of vinyl acetate.

20 Claims, No Drawings

CATALYST, PROCESS FOR ITS PRODUCTION AND ITS USE FOR PREPARING VINYL ACETATE

The present invention relates to a process for producing a catalyst by UV photoreduction of metal salts on a support, to the catalyst produced in this way and to its use for preparing vinyl acetate.

It is known that vinyl acetate can be prepared in the gas phase from ethylene, acetic acid and oxygen. The supported catalysts used for this synthesis comprise Pd and an alkali metal, preferably K. Further additives used are Cd, Au or Ba. The metal salts can be applied to the support by steeping, spraying on, vapor deposition, impregnation, dipping or precipitation.

In the case of the Pd/Au/K catalysts it has been found to be advantageous to apply the two noble metals in the form of a shell on the support, i.e. the noble metals are distributed only in a zone close to the surface while the regions lying further inside the shaped supported body are virtually free of noble metal. The thickness of these catalytically active shells is generally about 0.1–2 mm. Shell catalysts make it possible to carry out the process more selectively than in the case of catalysts in which the support particles are impregnated through to the core ("fully impregnated") or make it possible to increase the capacity. Here, the reaction conditions can be kept unchanged compared to the fully impregnated catalysts and more vinyl acetate can be produced for a given reactor volume and time. This makes the work-up of the crude vinyl acetate obtained easier, since the vinyl acetate content of the gas leaving the reactor is higher, which leads to an energy saving in the work-up section. Suitable work-ups are described, for example, in U.S. Pat. No. 5,066,365, DE-34 22 575, DE-34 08 239, DE-29 45 913, DE-26 10 624 and U.S. Pat. No. 3,840,590. On the other hand, if the plant capacity is kept constant, the reaction temperature can be lowered and the reaction can thus be carried out more selectively at the same total output, resulting in raw material savings. This also reduces the amount of the carbon dioxide which is formed as by-product and therefore has to be discharged and consequently reduces the loss of entrained ethylene associated with this discharge. In addition, this method of operation leads to a lengthening of the operating life of the catalyst.

Many documents disclose catalysts and processes for preparing vinyl acetate and processes for their production. These are fully impregnated catalysts or shell catalysts which are generally subjected to a chemical reduction of the noble metal compounds applied to the support to deposit the noble metals on the catalyst support. It has surprisingly been found that the catalytically active metals can also be deposited on the support by photoreduction.

The deposition of a metal on the surface of a support can be carried out from a gas, a liquid or an adsorbed surface layer. Such processes are described for many metals (including Ni, Ag, Au, Pd, Pt, Os and Ir) in the publications "Laser Processing and Chemistry" (Springer-Verlag, Berlin-Heidelberg-N.Y., 1996) and "Chemical Processing with Lasers" (Springer-Verlag, Berlin-Heidelberg-N.Y., 1986) by D. Bäuerle.

In terms of the process of the invention, the deposition of catalytically active metals from adsorbed surface layers is of particular interest.

W. Kräuter, D. Bäuerle, F. Fimberger, Appl. Phys. A 31, 13 (1983) describe the laser-induced deposition of Ni from the gas phase ($Ni(CO)_4$) using a krypton ion laser having wavelengths of from 476 to 647 nm. The substrate used was glass or Si. It is pointed out that the commencement of the deposition is attributable to the photoreduction of an adsorbed $Ni(CO)_4$ layer. This photoreduction is significantly more efficient when ultraviolet (UV) light is used than when visible light is used.

Y. -F. Lu, M. Takai, S. Nagatomo, K. Kato and S. Namba, Appl. Phys. A 54, 51–56 (1992) describe the deposition of Ag from an adsorbed silver acetate layer on a manganese-zinc ferrite substrate. An argon ion laser having a wavelength of 514.5 nm was used for the irradiation.

R. C. Sausa, A. Gupta and J. R. White, J. Electrochem. Soc. 134, 2707–2713 (1987) describe the deposition of Pt onto quartz from an organometallic layer, likewise by irradiation using an argon ion laser. The layer was produced by evaporation of the solvent from a solution containing the organometallic compound (Bright Platinum-05X, Engelhard Corporation) plus varnish-like binders and solvents. The deposited Pt was used as nucleating layer for electroless deposition of copper.

H. Esrom, J. Demmy and U. Kogelschatz, Chemtronics 4, 202–208 (1989) report the use of an $Xe_2^*$ excimer lamp (wavelength 172 nm) for depositing Pd nuclei on aluminum oxide substrates for the electroless deposition of copper. The adsorbed layer used was palladium acetate.

Y. Zhang and M. Stuke, Chemtronics 4, 212–215 (1989) also describe the deposition of Pd from a palladium acetate layer on aluminum oxide ceramics, quartz substrates and silicon wafers. The synchrotron radiation having a wavelength range of 40–400 nm from an electron synchrotron was used for irradiation.

H. Esrom and G. Wahl, Chemtronics 4, 216–223 (1989) describe the photoreduction of palladium acetate by irradiation with light from an ArF excimer laser (wavelength 193 nm) and a KrF excimer laser (wavelength 248 nm). This process was used to deposit Pd nuclei for the electroless deposition of copper on quartz and aluminum oxide ceramics.

A. G. Schrott, B. Braren and R. Saraaf, Appl. Phys. Lett. 64, 1582–1584 (1994) report the photoreduction of $PdSO_4$ to metallic Pd using an excimer laser. Here too, it could be shown that nucleated substrates ($SiO_2$) could be used for electroless deposition of copper.

P. B. Comita, E. Kay, R. Zhang and W. Jacob, Appl. Surf. Sci. 79/80, 196–202 (1994) describe the laser-induced coalescence of gold clusters in a thin fluorocarbon layer which has been produced by plasma polymerization. During the production of this layer, gold was embedded by ion sputtering. The polymer matrix was broken up and vaporized by irradiation with an argon ion laser to leave coherent gold structures.

None of these publications discloses a process for producing catalysts.

The photoinduced deposition of noble metals from adsorbed surface layers has been carried out using both UV light sources and light sources which emit visible light. Since the absorption coefficients of the materials used in the process of the invention are significantly higher in the ultraviolet spectral region than in the visible spectral region, correspondingly lower power densities can be employed if UV light sources are used. Since a significantly higher throughput is achieved in this way, the use of UV light sources is preferred. The sources having the shortest wavelengths generally display the highest efficiency and their use is therefore particularly preferred.

The UV radiation sources used for the photoreduction are prior art. They are lamps, lasers or other radiation sources such as synchrotrons or plasma discharger. Lamps which can be used are, in particular, Hg vapor lamps (with strong emission lines at wavelengths of 185 nm and 254 nm) and narrow-spectrum excimer lamps in which the UV radiation arises from the disintegration of excimers or exciplexes such as $Kr_2^*$ (wavelength 146 nm), $Xe_2^*$ (172 nm), $KrCl^*$ (222 nm) or $XeCl^*$ (308 nm). As high-power UV lasers, use is made of pulse excimer lasers. Here too, the light arises from the disintegration of excimers or exciplexes such as $F_2^*$ (157 nm), $ArF^*$ (193 nm), $KrF^*$ (248 nm), $XeCl^*$ (308 nm) and $XeF^*$ (351 nm). It is also possible to use frequency-multiplied Nd-YAG lasers (wavelength 1064 nm/n; n=3, 4, 5, . . . ). Further sources of UV radiation are synchrotrons which produce broad-band radiation extending into the X-ray region and the light of a plasma discharge at low pressure.

It is an object of the present invention to provide a process for producing shell catalysts which comprise noble metals, which process does not use chemical reducing agents and allows the shell thickness to be adjusted in a simple way. It is a further object of the present invention to produce an active and selective vinyl acetate shell catalyst based on Pd/Au quickly and inexpensively using few process steps while making it possible to control the shell thickness in a simple manner.

According to the invention, these objects are achieved by noble metal salts on a support being reduced to the metal and fixed in an outer shell of the shaped support body by means of photoreduction using UV radiation. The shell thickness can be adjusted via the penetration depth of the UV radiation. In this way, good uniformity of the catalytically active metal particles, a narrow particle size distribution and high dispersion of metal in the shell are achieved.

The present invention provides a process for producing shell catalysts comprising noble metals on a porous support, which comprises impregnating the support with salt solutions of the nobel metals and subsequently exposing it to UV radiation so that the metal salts in the zone close to the surface are reduced to the metals.

The photoreduction is preferably carried out using monochromatic UV excimer radiation. The process is preferably carried out in the absence of chemical reducing agents.

The metal salts in the interior of pellet which have not been irradiated and therefore have not been reduced are extracted by means of a solvent after irradiation of the support. The nanosize particles of nobel metal fixed in the shell are, owing to their insolubility, not washed out and remain fixed in position.

The invention further provides the shell catalysts which can be produced by this process.

The shell catalysts produced in this way can be used for many heterogeneously catalyzed reactions such as hydrogenations and oxidations.

Pd/Au shell catalysts produced by this process are suitable for use in the synthesis of vinyl acetate. Compared to conventional preparation techniques for supported noble metal catalysts (impregnation with metal salts and chemical reduction thereof), the photoreduction according to the invention makes it possible to omit the chemical reducing agent and thus avoid the associated disadvantages such as contamination of the support with extraneous metals, disposal of the salt formed, multistage operation and energy-intensive and time-consuming handling of often toxic solutions.

Compared to the conventional processes for producing a shell (fixing by means of base precipitation followed by chemical reduction), the process of the invention has the advantage that the shell thickness can be readily controlled and monitored via the the physical parameters significant in the deposition, e.g. wavelength and power of the UV radiation source, and also concentration of the impregnation solution and time and temperature of the photoreduction. In the process of the invention, the reduction and fixing in the shell occur simultaneously in one step.

Preference is given to catalysts having a shell thickness of from 5 to 5000 $\mu$m. Furthermore, preference is given to those catalysts which comprise Pd and/or Au.

The photoreduction according to the invention takes only a few minutes, while the conventional base fixing requires about 20 hours.

Owing to the properties mentioned, the shell catalysts produced according to the invention have high activities and selectivities.

As active metals which can be concentrated in the shell, all metals for which photoreducible precursors exist are suitable. A prerequisite for this is sufficient UV absorption by the precursors at the wavelength used for irradiation. Appropriate selection of the wavelength used for the irradiation enables UV absorption to be achieved for many simple and readily available metal salts such as acetates, formates, propionates, butyrates, nitrates, sulfates or chlorides. The impregnated supports can also be treated with sensitizers before irradiation with UV light. Owing to their ready photoreducibility, all noble metals and their mixtures are particularly suitable. Preference is given to Pd, Au, Pt, Ag, Rh, Ru, Os and Ir. Particular preference is given to Pd and Au.

Supports used are inert materials such as $SiO_2$, $Al_2O_3$, $TiO_2$, $ZrO_2$ or mixtures of these oxides in the form of spheres, pellets, rings, stars or other shaped bodies. The diameter or the length and thickness of the support particles is generally from 3 to 9 mm. The surface of the support is generally 10–500 $m^2/g$, preferably 20–250 $m^2/g$, as measured by the BET method. The pore volume is generally from 0.3 to 1.2 ml/g.

The reduction and fixing to the support of the noble metal precursors is, according to the invention, carried out by means of UV light. It is possible to use, for example, the following UV radiation sources: UV excimer lasers, frequency-multiplied Nd:YAG laser, UV excimer lamps, Hg vapor lamps, synchrotrons or low-pressure plasma dischargers. Preference is given to using UV excimer radiation which is monochromatic and has high power peaks. Suitable wavelengths are in the range from 40 to 400 nm. Preferred wavelengths are from 140 to 360 nm, in particular 172 nm ($Xe_2^*$ lamp), 193 nm ($ArF^*$ laser), 222 nm ($KrCl^*$ lamp), 248 nm ($KrF^*$ laser) and 308 nm ($XeCl^*$ lamp). Preferred UV power densities are from 0.01 to 100 $W/cm^2$, particularly preferably UV power densities of from 0.1 to 20 $W/cm^2$.

When pulsed lasers are used, suitable pulse frequencies are generally in the range from 0.1 to 5000 pulses/s. The irradiation times are generally from 0.01 s to 3600 s. Preferred pulse frequencies are from 1 to 1000 pulses/s and preferred irradiation times are from 0.01 to 1000 s, in particular from 0.1 to 300 s.

When using UV lamps which are not pulsed and can have significantly greater spatial and spectral irradiation windows than UV lasers, suitable irradiation times are from 1 s and 10 h. Preferred irradiation times are from 0.1 min to 100 min.

As a result of the limited penetration depth of the UV radiation, the thickness of the shell can be set and controlled easily.

If a plurality of noble metals are to be fixed to the support (e.g. Pd and Au), these can be photoreduced simultaneously according to the process of the invention by means of appropriate selection of the physical parameters significant in the deposition. This generally results in alloy particles. As an alternative, it is also possible to carry out sequential photoreduction under irradiation conditions optimized for each of the individual metals, which can lead to structured noble metal particles.

The photoreduction can also be combined with conventional chemical reduction. For example, the photoreduction can be used only for preliminary creation of the nuclei in the shell, which is then reinforced by renewed impregnation with the same or other metal salts and chemical reduction of these. Likewise, it is also possible to photoreduce only one of the two metals and subsequently to apply and reduce the other metal using conventional methods. For example, the support can first be impregnated with palladium acetate which is then phototreduced in a shell to give Pd metal. The support can then be further impregnated with Au salts which can be reduced wet chemically or else in situ in the reactor using gaseous reducing agents such as $H_2$ or ethylene. This ensures that the actual active metal for the vinyl acetate process, i.e. the Pd, is fixed in a shell, while the distribution of the activator, i.e. the Au, is less critical and it can therefore be fixed using conventional chemical methods.

The noble metal salts in the interior of the pellet which have not been irradiated and therefore have not been reduced are extracted by means of a solvent. Suitable solvents are, for example, chloroform, acetic acid or aqueous solutions of citric acid or oxalic acid.

The process of the invention is particularly suitable for producing vinyl acetate shell catalysts. There are 3 types of these, which are composed essentially of Pd/Cd/K, Pd/Ba/K or Pd/Au/K. The finished vinyl acetate catalysts have the following compositions:

The Pd content of the Pd/K/Cd and the Pd/K/Ba catalysts is generally from 0.6 to 3.5% by weight, preferably from 0.8 to 3.0% by weight, in particular from 1.0 to 2.5% by weight. The Pd content of the Pd/Au/K catalysts is generally from 0.5 to 2.0% by weight, preferably from 0.6 to 1.5% by weight.

The K content of all three types of catalysts is generally from 0.5 to 4.0% by weight, preferably from 1.5 to 3.0% by weight.

The Cd content of the Pd/K/Cd catalysts is generally from 0.1 to 2.5% by weight, preferably from 0.4 to 2.0% by weight.

The Ba content of the Pd/K/Ba catalysts is generally from 0.1 to 2.0% by weight, preferably from 0.2 to 1.0% by weight.

The Au content of the Pd/K/Au catalysts is generally from 0.2 to 1.0% by weight, preferably from 0.3 to 0.8% by weight.

Suitable salts are all salts of palladium, cadmium, barium, gold and potassium which are soluble and contain no constituents which act as catalyst poisons, e.g. sulfur. Preference is given to the acetates and the chlorides. However, in the case of the chlorides, it has to be ensured that the chloride ions are removed before the catalyst is used. This is achieved by washing the doped support, e.g. with water, after Pd and, if desired, Au have been fixed on the support by reduction to the metal particles.

Suitable solvents for the impregnation are all compounds in which the salts selected are soluble and which can be easily removed again by drying after the impregnation. Suitable solvents for the acetates are first and foremost unsubstituted carboxylic acids, in particular acetic acid. For the chlorides, water is especially suitable. The additional use of a further solvent is advantageous when the salts are not sufficiently soluble in the acetic acid or in the water. Suitable additional solvents are those which are inert and miscible with acetic acid or water. Examples of additives for acetic acid are ketones such as acetone and acetylacetone, also ethers such as tetrahydrofuran or dioxane, acetonitrile, dimethylformamide and also hydrocarbons such as benzene.

In general, at least one salt of each of the elements (Pd/K/Au, Pd/K/Cd, Pd/K/Ba) to be applied to the support particles is applied. It is possible to apply a plurality of salts of one element, but it is usual to apply only one salt of each of the three elements. The necessary amount of salt can be applied in one step or by multiple impregnation. The salts can be applied to the support by known methods such as steeping, spraying on, vapor deposition, dipping, impregnation or precipitation.

In the process of the invention, only the noble metal salts, i.e. Pd and Au salts, are reduced to the corresponding nanosize noble metal particles and the "base" constituents K, Cd, Ba are not reduced. The latter can be applied to the support together with the noble metal salts or else beforehand or afterwards. In the process of the invention, it is usual to first produce a shell of Pd/Au and then to impregnate the support with potassium acetate solution, giving a uniform distribution of K over the pellet cross section.

Vinyl acetate is generally prepared by passing acetic acid, ethylene and oxygen or oxygen-containing gases at temperatures of from 100 to 220° C., preferably from 120 to 200° C., and at pressures of from 1 to 25 bar, preferably from 1 to 20 bar, over the finished catalyst, with unreacted components being able to be circulated. The oxygen concentration is advantageously kept below 10% by volume (based on the gas mixture without acetic acid). Dilution with inert gases such as nitrogen or carbon dioxide may also be advantageous under some circumstances. Carbon dioxide is particularly suitable for dilution since it is formed in small amounts during the reaction.

The following examples illustrate the invention.

EXAMPLE 1 a) Impregnation of porous $SiO_2$ pellets with palladium acetate:

50 ml (about 25 g) of Aerosil 200 pellets (5.5×6 mm, Degussa) are placed in a flask. 530 mg of palladium acetate (Aldrich) are dissolved in 30 ml of glacial acetic acid (corresponds to 1% by weight of Pd). The solution is filtered through a fluted filter paper. The clear Pd solution is added to the Aerosil pellets and the glacial acetic acid is taken off again over a period of 2 hours on a rotary evaporator with continuous rotation. Remaining acetic acid is subsequently taken off in an oil pump vacuum at 0.2 mbar/60° C.

b) Photoreduction:

The end faces of the pellets were irradiated in air by means of a KrF* laser (wavelength 248 nm) using 500 laser pulses in each case. The energy density of the laser on the specimen surface was 350 mJ/cm$^2$. The pulse frequency of the laser was 10 pulses/s. After cutting a representative number of pellets, the shell thickness was measured by means of optical microscopy and XPS line scans. The shell thickness is about 0.5 mm.

c) Conversion into the industrial catalyst:

20 ml of irradiated Aerosil pellets are washed with 2 l of acetic acid, 40%+10% of potassium acetate, in a Soxhlet extractor and dried at 110° C. Since the pellets already contain 1% of Pd, only Au is applied here: 125.4 mg of Au(CH$_3$COO)$_3$ (corresponds to 66 mg of Au), prepared by the method of U.S. Pat. No. 4,933,204, are dissolved in 1 0mi of H$_2$O and added to the pellets. The solution is evaporated on a rotary evaporator with rotation and under a stream of N$_2$. The pellets are then dried at 110° C. 0.8 g of potassium acetate is dissolved in 15 ml of H$_2$O and applied to the pellets as above, dried at 110° C. for 4 hours then additionally dried overnight under reduced pressure.

d) Reactor tests

Reactor tests on the gas phase oxidation of ethylene and acetic acid to give vinyl acetate:

The catalysts are tested in a fixed-bed tube reactor having a tube diameter of 2 cm. The reactor is heated externally by means of oil jacket heating. 15 ml of the shaped catalyst bodies are placed in the reactor. The reactor volume upstream and downstream of the catalyst bed is filled with glass spheres. The test apparatus is controlled by a process control system and is operated continuously. The catalyst is first activated and then tested under constant reaction conditions.

Activation comprises a plurality of steps: heating under $N_2$, addition of ethylene, pressure increase, addition of acetic acid, holding of the conditions, addition of oxygen.

The reaction conditions during the test are 160–170° C. reaction temperature, 8–9 bar gauge pressure. The feed is composed of 64.5% by volume of ethylene, 16.1% by volume of $N_2$, 14.3% by volume of acetic acid and 5.1% by volume of $O_2$. A full analysis of the reactor output is carried out directly at the reactor outlet by means of on-line GC (2 column arrangement).

The test results are shown in the following table. The concentration ratios of the components are given in GC percentage areas.

TABLE 1

| | | | GC analysis of the reactor output | | | | | | |
|---|---|---|---|---|---|---|---|---|---|
| Catalyst | T (° C.) | p (bar) | $CO_2$ | $C_2H_4$ | $O_2$ | $N_2$ | $H_2O$ | Vinyl acetate | Acetic acid |
| Example 1 | 160 | 9 | 0.85 | 55.7 | 3.25 | 19.5 | 0.8 | 1.27 | 18.5 |
| Example 2 | 170 | 9 | 1.4 | 53.8 | 2.59 | 23.1 | 1.18 | 1.15 | 16.8 |

EXAMPLE 2 a) Impregnation of porous $SiO_2$ pellets with palladium acetate and gold acetate:

50 ml (about 25 g) of Aerosil 200 pellets (5.5×6 mm, Degussa) are placed in a flask. 530 mg of palladium acetate (Aldrich) (corresponds to 1% by weight of Pd) are dissolved in 30 ml of glacial acetic acid. 290 mg of gold acetate (corresponds to 0.6% by weight of Au), prepared by the method of U.S. Pat. No. 4,933,204, are dissolved in 10 ml of glacial acetic acid. The two solutions are combined and filtered through a fluted filter paper. The clear Pd/Au solution is added to the Aerosil pellets and the glacial acetic acid is taken off again over a period of 2 hours on a rotary evaporator with continual rotation. Remaining acetic acid is subsequently taken off in an oil pump vacuum at 0.2 mbar/60° C. The final weight of the impregnated pellets is 25.8 g.

b) Photoreduction:

The impregnated tablets were irradiated on both end faces in air by means of a KrF* laser (wavelength 248 nm) using 150 laser pulses in each case. The energy density (flux) of the laser light on the specimen surface was 350 mJ/cm². The pulse frequency of the laser was 10 pulses/s.

After cutting a representative number of pellets, the shell thickness was measured by means of optical microscopy and XPS line scans. The number of pulses is selected so that the shell thickness is about 0.9 mm.

The color change from yellow to black/brown induced by the irradiation could be seen clearly. In contrast to Example 1 (preimpregnation only with palladium acetate), a color change could be achieved more easily in the case of the Pd/Au preimpregnation.

c) Conversion into the industrial catalyst

The irradiated tablets are washed in a Soxhlet extractor first with 2000 ml of 40% acetic acid and then with 1000 ml of water, dried overnight at 110° C. under atmospheric pressure and then dried for another 1 hour under reduced pressure. 2 g of potassium acetate are dissolved in 30 ml of water and added all at once to the pellets. The solution and pellets are mixed for 15 min with continual rotation and are again dried at 110° C. under atmospheric pressure, finally for another 1 hour under reduced pressure.

d) Reactor tests

The preparation of vinyl acetate was carried out under the same conditions as indicated under d) in Example 1. The test results are shown in the following table. The concentration ratios of the components are given in GC percentage areas:

TABLE 2

| | | | GC analysis of the reactor output | | | | | | |
|---|---|---|---|---|---|---|---|---|---|
| Catalyst | T (° C.) | p (bar) | $CO_2$ | $C_2H_4$ | $O_2$ | $N_2$ | $H_2O$ | Vinyl acetate | Acetic acid |
| Example 2 | 160 | 9 | 0.01 | 56.8 | 4.3 | 19.5 | 0.06 | 0.34 | 19.0 |

What is claimed is:

1. A process for producing shell catalysts comprising noble metals on a porous support, which comprises:
   impregnating the support with salt solutions of the noble metals;
   exposing the support to UV radiation so that the noble metals in the zone close to the surface are reduced to metals; and
   extracting the pellets in a solvent in order to remove the noble metal salts in the interior of the pellet which have not been irradiated.

2. The process as claimed in claim 1, wherein the noble metals are selected from the group consisting of Pd, Au, Pt, Ag, Rh, Ru, Os and Ir.

3. The process as claimed in claim 1 wherein the noble metals are Au and Pd and the salts thereof which are used are the acetates.

4. The process as claimed in one of claims 1 to 3, wherein the support material used is $SiO_2$, $Al_2O_3$, $TiO_2$, $ZrO_2$ or a mixture thereof.

5. The process as claimed in one of claims 1 to 3, wherein the UV photoreduction is carried out by irradiation with light having a wavelength of from 40 to 400 nm.

6. The process as claimed in claim 5, wherein the UV photoreduction is carried out by irradiation with light having a wavelength of from 140 to 360 nm.

7. The process as claimed in one of claims 1 to 3, wherein the photoreduction of the Pd and/or Au is carried out by irradiation with UV light having a power density of from 0.01 to 100 W/cm$^2$ from a lamp or a pulsed laser, where, when a pulsed laser is used, the pulse frequency is from 1 to 1000 pulses/s and the irradiation time is from 0.01 to 1000 s, while when a lamp is used the irradiation time is from 0.1 min to 100 min.

8. The process as claimed in claim 7, wherein the UV light has a power density of from 0.1 to 20 W/cm$^2$.

9. The process as claimed in one or more of claims 1 to 3, wherein the impregnated catalyst support is treated with UV sensitizers before irradiation.

10. The process as claimed in one of claims 1 to 3 carried out without using a chemical reducing agent.

11. A shell catalyst obtainable by the process as claimed in one of claims 1 to 3, wherein the shell thickness is from 5 to 5000 μm.

12. A shell catalyst as claimed in claim 11, wherein the noble metals present are Pd and/or Au.

13. A shell catalyst obtainable by the process of claim 9, wherein the shell thickness is from 5 to 5000 μm.

14. A shell catalyst obtainable by the process of claim 8, wherein the shell thickness is from 5 to 5000 μm.

15. A shell catalyst obtainable by the process of claim 10, wherein the shell thickness is from 5 to 5000 μm.

16. A process for hydrogenation or oxidation reactions in the presence of a catalyst obtainable by a process as claimed in one or more of claims 1 to 3.

17. A process for preparing vinyl acetate in the gas phase from ethylene, acetic acid and oxygen or oxygen-containing gases in the presence of a catalyst obtainable by a process as claimed in one of claims 1 to 3.

18. A process for preparing vinyl acetate in the gas phase from ethylene, acetic acid and oxygen or oxygen-containing gases in the presence of a catalyst obtainable by a process as claimed in claim 11.

19. A process for preparing vinyl acetate in the gas phase from ethylene, acetic acid and oxygen or oxygen-containing gases in the presence of a catalyst obtainable by a process as claimed in claim 8.

20. A process for preparing vinyl acetate in the gas phase from ethylene, acetic acid and oxygen or oxygen-containing gases in the presence of a catalyst obtainable by a process as claimed in claim 10.

* * * * *

UNITED STATES PATENT AND TRADEMARK OFFICE
CERTIFICATE OF CORRECTION

PATENT NO.     : 6,268,522 B1
DATED          : July 31, 2001
INVENTOR(S)    : Hagemeyer et al.

It is certified that error appears in the above-identified patent and that said Letters Patent is hereby corrected as shown below:

Column 8,
Line 54, insert -- at elevated temperatures -- after "in a solvent".

Column 9,
Line 24, "claim 9" should read -- claim 7 --.

Signed and Sealed this

Twenty-sixth Day of March, 2002

Attest:

JAMES E. ROGAN
Attesting Officer   Director of the United States Patent and Trademark Office